United States Patent [19]

Galy et al.

[11] Patent Number: 5,184,450
[45] Date of Patent: Feb. 9, 1993

[54] METHOD OF PACKAGING FREEZE DRIED VACCINES IN SYRINGES AND PLUG FOR IMPLEMENTING THE METHOD

[75] Inventors: Michel G. H. Galy, Pontchara-sur-Turdine; Alain Gomez, Lyons, both of France

[73] Assignee: Pasteur Merieux Serums et Vaccins, France

[21] Appl. No.: 836,615

[22] Filed: Feb. 18, 1992

[30] Foreign Application Priority Data

Feb. 15, 1991 [FR] France ................ 91 01802

[51] Int. Cl.⁵ .............. B65B 31/04; B65B 7/28; B67C 3/00; A61M 5/19
[52] U.S. Cl. .......................... 53/440; 53/127; 53/237; 53/474; 53/489; 604/191
[58] Field of Search ............ 53/440, 489, 485, 474, 53/127, 237, 284.6, 319, 287; 604/191, 226, 228

[56] References Cited

U.S. PATENT DOCUMENTS

| | | | |
|---|---|---|---|
| 3,348,546 | 10/1967 | Roberts et al. | 53/489 X |
| 4,716,710 | 1/1988 | Galy et al. | 53/440 X |
| 4,792,329 | 12/1988 | Schreuder | 604/191 X |
| 4,874,381 | 10/1989 | Vetter | 604/191 |
| 4,968,299 | 11/1990 | Ahlstrand et al. | 604/191 X |
| 4,994,043 | 2/1991 | Ysebaert | 604/191 |

FOREIGN PATENT DOCUMENTS

| | | |
|---|---|---|
| 0397977 | 3/1990 | Fed. Rep. of Germany . |
| 223990 | 3/1975 | France . |

*Primary Examiner*—James F. Coan
*Attorney, Agent, or Firm*—Larson and Taylor

[57] ABSTRACT

In a method of packaging freeze dried vaccine in a bypass syringe sterilized syringes are disposed in rows in an aseptic dispensing machine. Doses of a solution or suspension to be freeze dried are introduced into the syringes. A temporary plug is inserted in the same machine into the mouth of the syringe body in a position allowing communication between the interior of the syringe body and the exterior. The syringes are introduced into a freeze drying machine. The vaccine is freeze dried. At the end of the freeze drying cycle the temporary plug is depressed in a controlled atmosphere in the freeze drying machine into a hermetic sealing position. The syringes are transferred into an aseptic dispensing machine. The temporary plug is removed. An intermediate piston-plug is fitted. The dose of solvent is introduced and an end piston-plug is fitted.

9 Claims, 5 Drawing Sheets

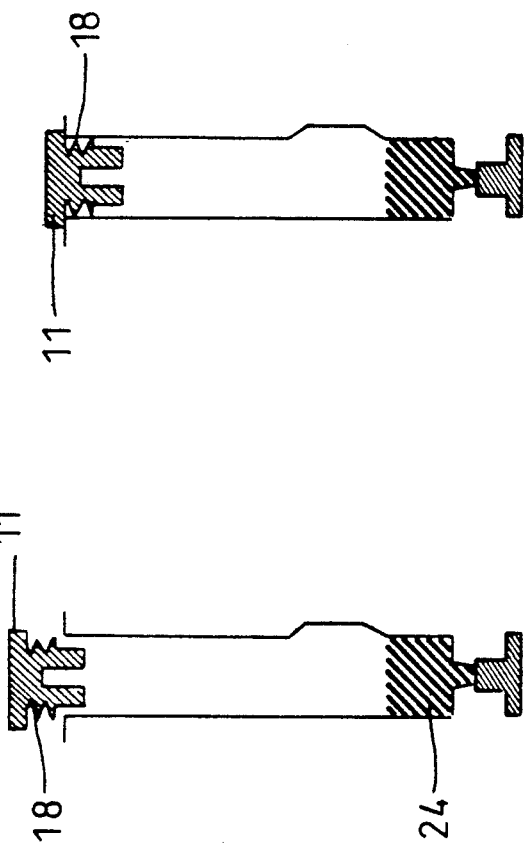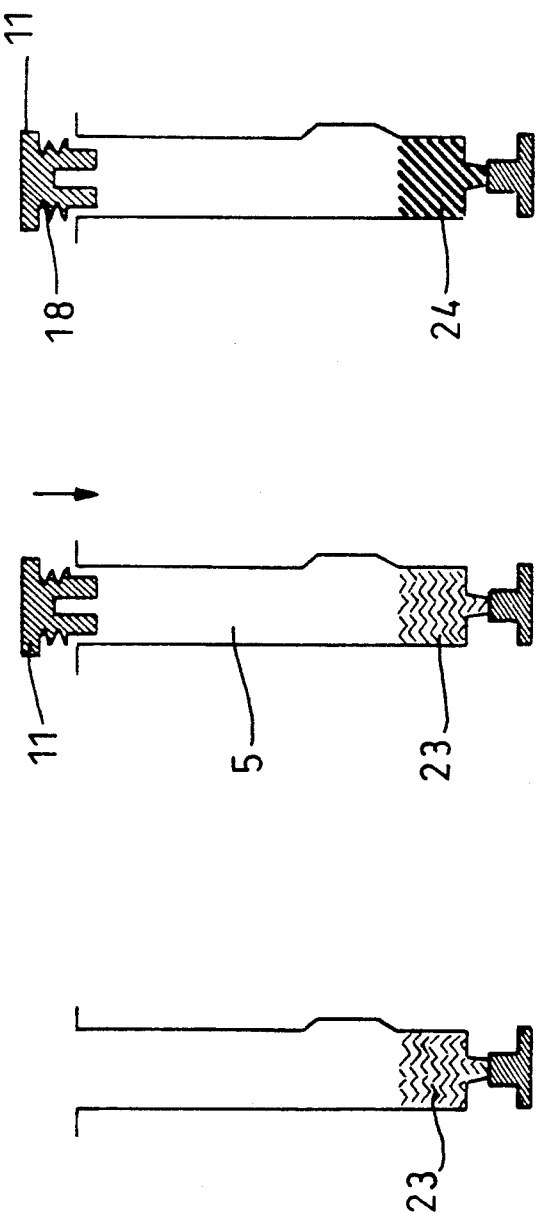

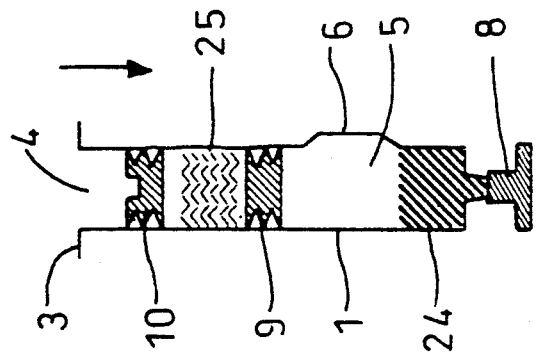
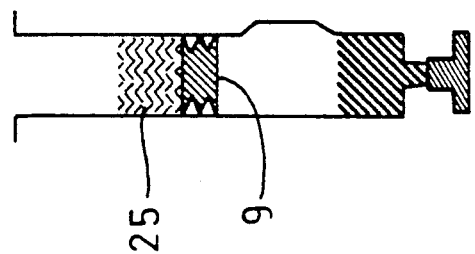
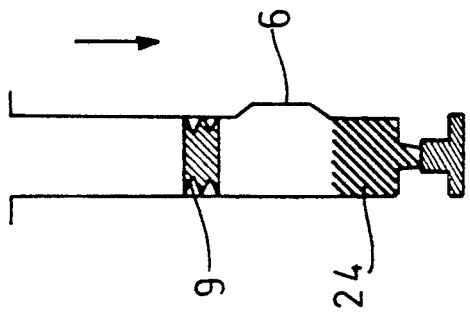
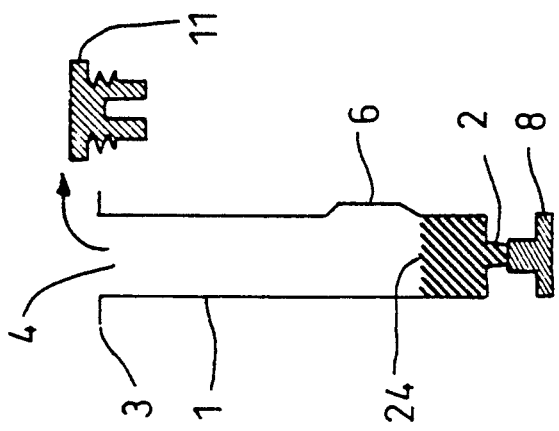
FIG. 9

METHOD OF PACKAGING FREEZE DRIED VACCINES IN SYRINGES AND PLUG FOR IMPLEMENTING THE METHOD

BACKGROUND OF THE INVENTION

1. Field of the Invention

The present invention concerns a method of packaging freeze dried vaccines in syringes and a plug for implementing the method.

2. Description of the Prior Art

So-called bypass syringes designed to contain a freeze dried active substance and a solvent are already known. Generally made from glass, these syringes have a generally cylindrical syringe body with a passage leading to the needle in the anterior part and a piston-plug in the posterior part coupled to a piston rod actuated by the user. The cylindrical cavity inside the body is divided into two parts, namely an anterior part containing the freeze dried active substance and a posterior part separated from the anterior part by an intermediate piston-plug and containing the solvent. A bypass is provided by a localized longitudinal rib in the glass. In an initial position the bypass communicates with the anterior part containing the freeze dried active substance and is inaccessible to the liquid because of the presence of the intermediate piston-plug. When the user depresses the end piston-plug the liquid depresses the intermediate piston-plug until it uncovers the bypass whereupon the liquid is expelled into the first part containing the freeze dried active substance. The dissolved active substance is expelled from the syringe through the needle after the two pistons come into contact.

However, these syringes are not generally used for freeze dried vaccines because these vaccines are extremely fragile, very sensitive to the relative humidity and temperature of their surroundings, so that it is not possible to carry out under industrial conditions in situ freeze drying in a freeze drying machine followed by fitting of the intermediate piston-plug and filling in a second, so-called dispensing machine because of the breakdown in the continuity of the environment. As a result freeze dried vaccines such as the particularly fragile Haemophilus vaccine, for example, must be packaged in syringes with no solvent so that the medical or nursing personnel must first draw up the solvent from a bottle.

The present invention proposes to remedy these drawbacks and to enable the packaging of fragile freeze dried vaccines in bypass syringes without compromising the quality of the vaccine.

Another objective of the invention is to implement this process using conventional freeze drying installations and conventional dispensing installations or installations which require only minor and temporary modification.

SUMMARY OF THE INVENTION

In one aspect, the present invention consists in a method of packaging freeze dried vaccine in a bypass syringe in which sterilized syringes are disposed in rows in an aseptic dispensing machine, doses of a solution or suspension to be freeze dried are introduced into said syringes, a temporary plug is inserted in the same machine into the mouth of said syringe body in a position allowing communication between the interior of said syringe body and the exterior, said syringes are introduced into a freeze drying machine, the vaccine is freeze dried, at the end of the freeze drying cycle said temporary plug is depressed in a controlled atmosphere in said freeze drying machine into a hermetic sealing position, said syringes are transferred into an aseptic dispensing machine, said temporary plug is removed, an intermediate piston-plug is fitted, the dose of solvent is introduced and an end terminal piston-plug is fitted.

In the first phase of the process, in the laminar flow aseptic dispensing area of the first dispensing machine supplied with groups of syringes disposed in special strips or cassettes, the solution or suspension to be freeze dried is dispensed into the syringes after which the temporary plugs are fitted either in the machine or using another device. The temporary plugs can be inserted to the position allowing freeze drying using conventional methods.

After the cassettes of syringes are transferred into the freeze drying machine and freeze drying has been carried out the temporary plug is depressed in a controlled atmosphere in the freeze drying machine by simple displacement of a plate so that the closure is hermetically sealed although part of the temporary plug projects externally to allow cooperation with grasping means enabling it to be extracted in the aseptic dispensing area in which the automatic solvent dispensing machine is located.

The process has the further advantage of enabling syringes containing the freeze dried vaccine to be stored for as long as necessary before the solvent is added.

The temporary plug can be any suitable shape, preferably comprising three consecutive parts, namely a first part entering at least partially into the syringe body leaving passages enabling communication between the interior of the syringe and the exterior environment, a second part adapted to be inserted into the syringe body in a second insertion position of the plug to achieve hermetic sealing of the syringe body and a third part preferably projecting to the exterior in any position of the plug enabling the plug to be grasped and withdrawn from the syringe body.

In a preferred embodiment the temporary plug advantageously comprises three (for example) longitudinal ribs in said first part leaving between them passages for vapour and gas, the second part comprising a peripheral sealing rib or lip and the third part having means such as a peripheral groove enabling it to be grasped by an extractor tool.

The first part of the plug advantageously has an intermediate abutment relief portion enabling accurate positioning in the part-inserted freeze drying position, the abutment being sufficiently flexible to allow further insertion of the plug when a greater force is exerted.

In a second aspect, the present invention consists in a temporary plug for implementing a method of packaging freeze dried vaccine in a bypass syringe in which sterilized syringes are disposed in rows in an aseptic dispensing machine, doses of a solution or suspension to be freeze dried are introduced into said syringes, a temporary plug is inserted in the same machine into the mouth of said syringe body in a position allowing communication between the interior of said syringe body and the exterior, said syringes are introduced into a freeze drying machine, the vaccine is freeze dried, at the end of the freeze drying cycle said temporary plug is depressed in a controlled atmosphere in said freeze drying machine into a hermetic sealing position, said syringes are transferred into an aseptic dispensing machine, said temporary plug is removed, an intermediate piston-plug is fitted, the dose of solvent is introduced and an end terminal piston-plug is fitted, said temporary plug comprising a first part adapted to enter at least partially into said syringe body and said passages enabling communication between the interior of said syringe and the exterior environment, a second part adapted to be inserted into said syringe body in a second insertion position of said temporary plug to seal hermetically said syringe body, and a third part adapted to project to the outside in any position of said temporary plug to enable grasping of said temporary plug to remove it from said syringe body.

Other advantages and features of the invention will emerge from the following description given by way of non-limiting example only with reference to the appended drawings.

BRIEF DESCRIPTION OF THE DRAWINGS

FIG. 8 is a diagram showing four stages (FIGS. 8a–8d) of the method, stages 8a and 8b being carried out in a first or dispensing area and stages 8c and 8d in the freeze drying machine.

FIG. 9 is a diagram showing four consecutive stages (FIGS. 9a–9d) in a second or solvent dispensing area.

DETAILED DESCRIPTION OF THE INVENTION

Figure 1:
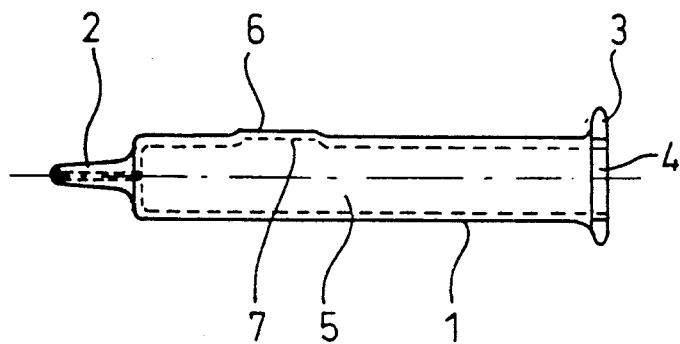
FIG. 1 is a view in elevation of a bypass syringe body.
Figure 2:
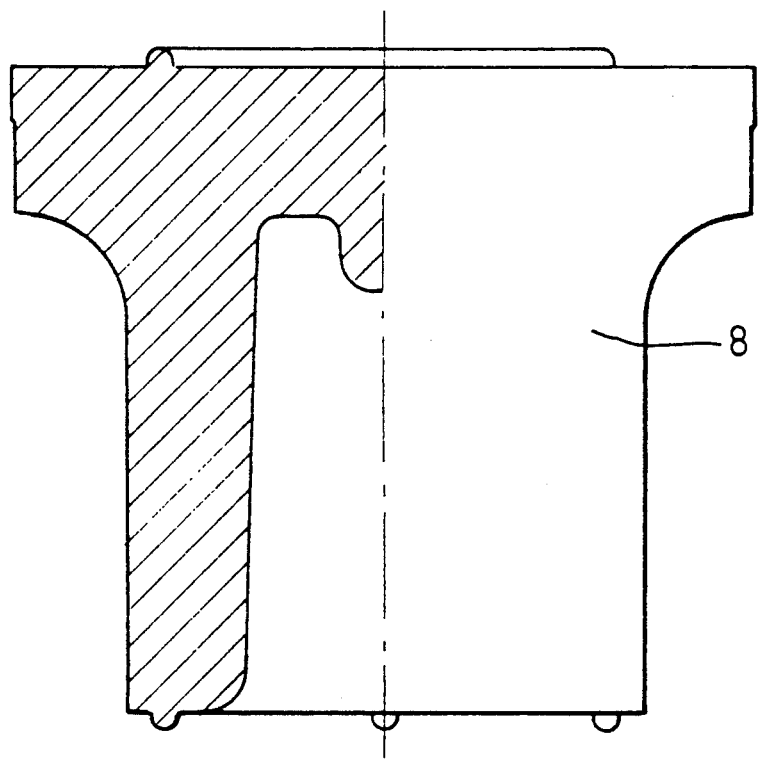
FIGS. 2, 3 and 4 are views in elevation and partially in cross-section of an end plug adapted to be fitted to the end of the syringe adapted to receive the needle, an intermediate or bypass plug and an end piston-plug.

Referring to all the figures:

According to the invention, freeze dried vaccine (Haemophilus vaccine, for example) is packaged in bypass syringes. FIG. 1 shows a bypass syringe made from glass and having a body 1 having at the front an end-piece 2 adapted to receive the needle and at the rear a conventional shoulder 3, the mouth 4 of the cylindrical internal cavity 5 having a peripheral lip forming a conventional small rib which very slightly reduces the diameter of the mouth 4 relative to the diameter of the cylindrical internal cavity 5. Approximately one third of the way in from the front end, a relatively short longitudinal rib 6 is blown whose inside forms a longitudinal bypass groove 7. Syringes of this design are available through ordinary trade channels.

The end plug 8 is fitted over the end-piece 2 to close off the passage in the end-piece and to seal the syringe at this end.

Figure 3:
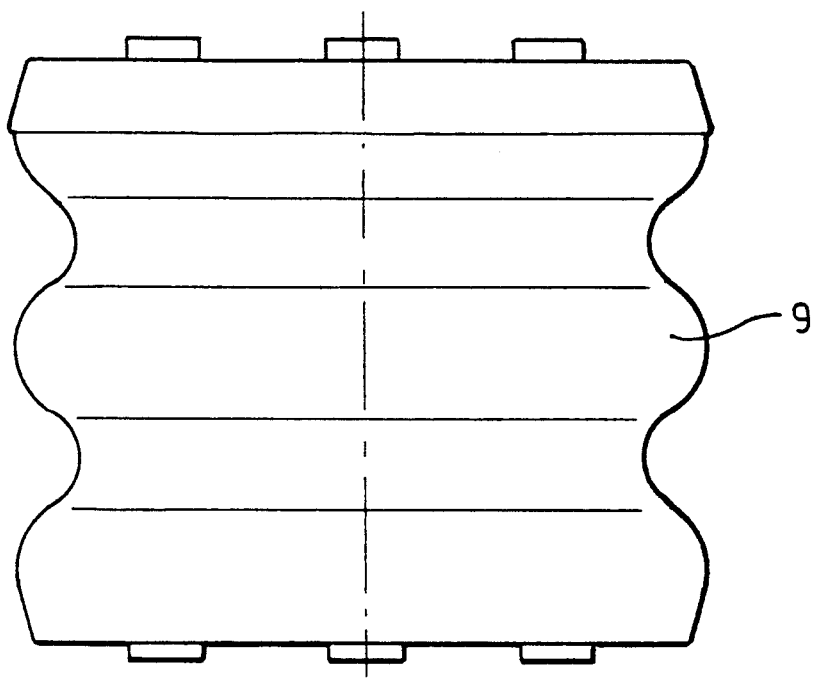
Figure 4:
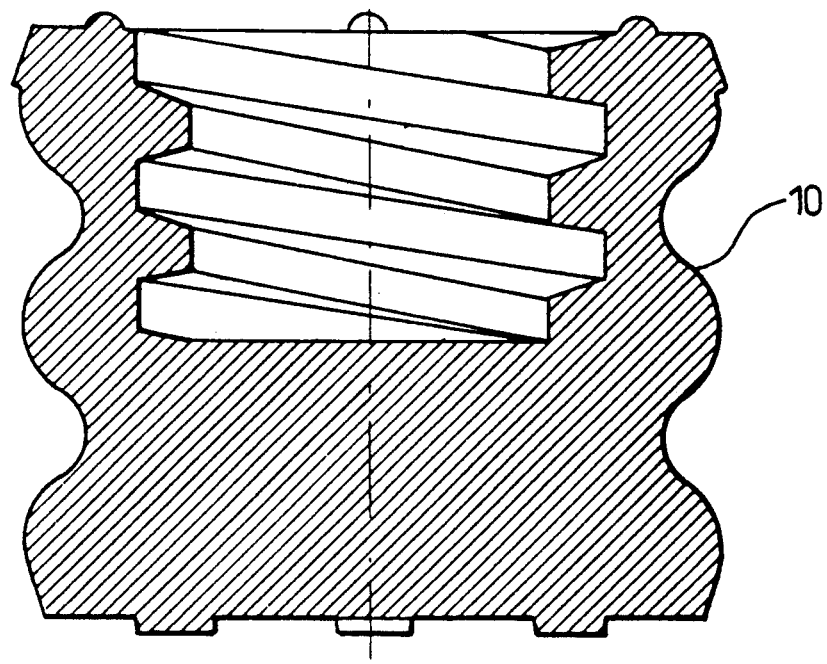

The bypass piston-plug 9 shown in FIG. 3 is also of a conventional type and is designed to separate the freeze dried vaccine in the anterior part of the body 5 from the solvent in the posterior part, the plug 9 sealing the rear end of the bypass 7 between the anterior part that it delimits and which contains the freeze dried vaccine and the posterior part containing the solvent. Finally, the end piston 10 is also of a conventional type and, as shown in FIG. 4, includes a screwthreaded posterior cavity into which a piston rod (not shown) can be screwed.

Figure 5:
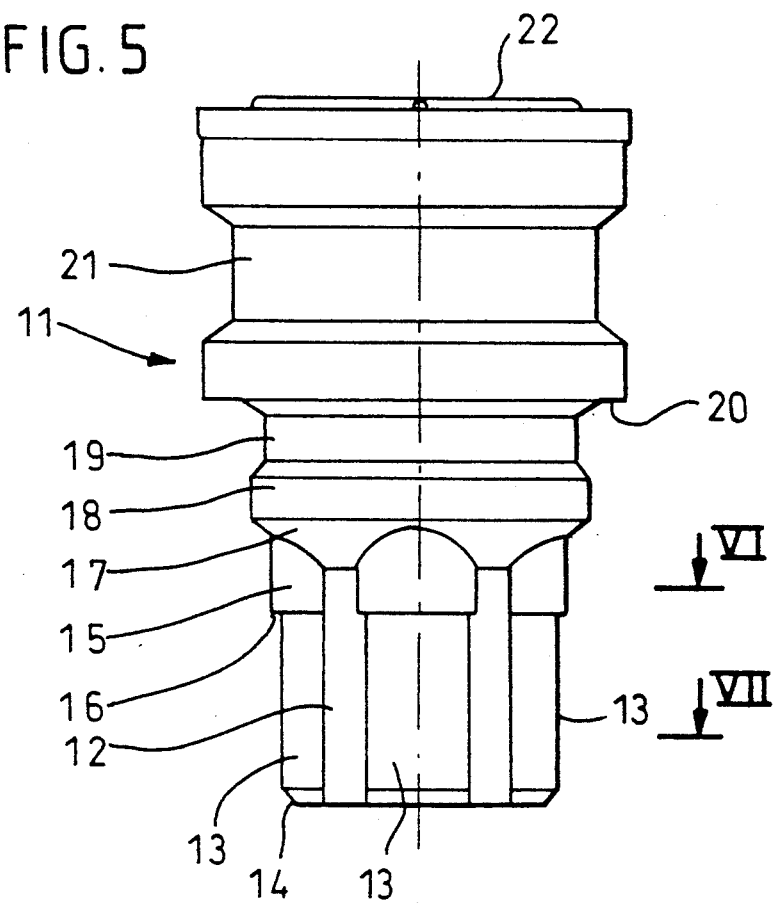
FIG. 5 is a view in elevation of a temporary plug in accordance with the invention.
Figure 6:
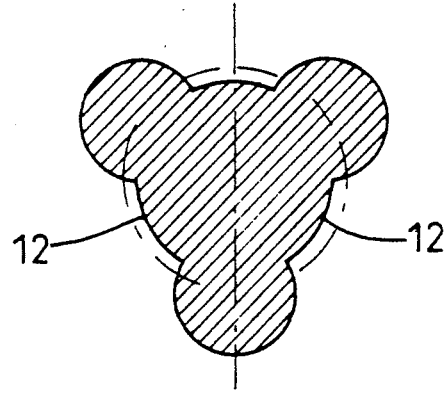
FIGS. 6 and 7 show the plug in cross-section on the lines VI—VI and VII—VII in FIG. 5.
Figure 7:
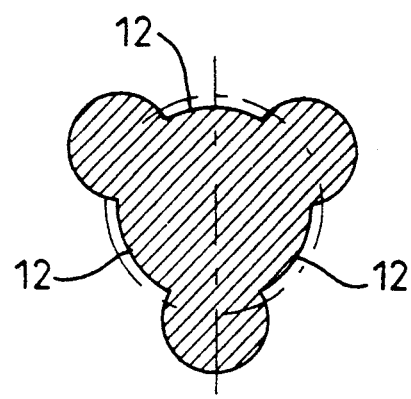

Referring to FIGS. 5 through 7, the temporary plug 11 is divided lengthwise into three functional parts.

The first is a small diameter generally cylindrical part 12 upstanding from which are three substantially cylindrical cross-section columns 13 whose ends 14 are slightly bevelled to facilitate insertion into the mouth of the syringe. These columns or ribs 13 are slightly thicker at their upper end 15 to form small shoulders 16 acting as abutments to determine an intermediate position of the plug 11. Above the part 15 of the columns 13 the plug has a frustoconical divergent portion 17 ending in a peripheral sealing rib 18. The overall radial dimension of the columns 13 is substantially equal to the diameter of the cavity 5 or of the mouth 4 so that the plug can be inserted with slight friction into the mouth. The diameter of the part 15 of the columns is slightly greater than the diameter of the mouth 4 so as to form an abutment and to determine a semi-inserted position in which the columns 12 are inside the syringe body while their part 15 remains outside so that a passage for gas and vapour between the interior of the syringe body and the surrounding environment is provided at the surfaces 12 and 17. The diameter of the rib 18 is sufficiently larger than the diameter of the mouth 4 and the cavity 5 that, when the plug is inserted further, the rib 18 provides a perfect seal at the mouth.

A part 19 of reduced diameter lies above the sealing rib 18. Above this the third part of the plug features a wide shoulder 20 determining the maximum insertion of the plug into the syringe body. Above the shoulder 20 is a groove 21 adapted to cooperate with a grasping tool which is used to extract the plug which is inserted by applying pressure to its upper end 22.

Referring to FIGS. 8 and 9:

This method in accordance with the invention of packaging the vaccine begins with washing, coating with silicone and autoclaving the plugs 9 and 10. The plugs 8 and 11 are also washed and then sterilized. On a conventional automated preparation machine the syringe bodies are disposed in series of 18 on compartmented strips after which the end plug 8 is automatically fitted. The next stage, also conventional, is to wash and coat with silicone the interior body of the syringes which are grouped together and then stowed in special cassettes which are then sterilized in the autoclave.

The sterilized cassettes are brought to a conventional laminar flow aseptic dispensing area and in stage 8a the various syringes in the cassette receive the dose 23 of liquid vaccine in a conventional dispensing machine. After the dose is dispensed into each syringe in the cassette the machine fits a temporary plug 11 to each syringe and inserts it until the shoulders 16 come into contact with the lip at the mouth so that insertion is limited and passages are left between the interior of the syringe body 5 and the exterior. The cassettes are then moved into the freeze drying machine. During the first stage 8c in the freeze drying machine freeze drying is carried out to produce the freeze dried vaccine 24. At the end of freeze drying, in stage 8d, the freeze drying machine plate is moved slightly so that the temporary plug 11 is depressed until the sealing rib 18 enters the body and seals it. The cassettes of syringes can then be taken out of the freeze drying machine and transported without requiring special precautions. In this condition they can be stored for long periods.

The cassettes containing the syringes with the freeze dried vaccine protected in this way are then taken to a second laminar flow aseptic dispensing area in which the temporary plugs 11 are extracted in stage 9a, optionally for recovery and recycling. To this end the machine may advantageously comprise forked fingers which are inserted into the groove 21 to remove the plug. Stage 9b, also carried out in this conventional machine, depresses the bypass piston plug to its position above the upper end of the bypass 6, thereby isolating the anterior part which contains the freeze dried vaccine 24. The dispensing machine then introduces into each syringe the dose 25 of solvent (stage 9c) after which (stage 9d) the end piston-plug 10 is fitted to complete the packaging process.

Although the invention has been described with reference to a specific embodiment, it is no way limited thereto, of course, and various modifications of shape or materials may be made thereto without departing from the scope or spirit of the invention.

There is claimed:

1. Method of packaging freeze dried vaccine in a bypass syringe in which sterilized syringes are disposed in rows in an aseptic dispensing machine, doses of a solution or suspension to be freeze dried are introduced into said syringes, a temporary plug is inserted in the same machine into the mouth of said syringe body in a position allowing communication between the interior of said syringe body and the exterior, said syringes are introduced into a freeze drying machine, the vaccine is freeze dried, at the end of the freeze drying cycle said temporary plug is depressed in a controlled atmosphere in said freeze drying machine into a hermetic sealing position, said syringes are transferred into an aseptic dispensing machine, said temporary plug is removed, an intermediate piston-plug is fitted, the dose of solvent is introduced and an end terminal piston-plug is fitted.

2. Method according to claim 1 wherein said temporary plug is depressed in a controlled atmosphere in said freeze drying machine by moving a plate of said freeze drying machine.

3. Method according to claim 1 wherein said temporary plug is extracted in a laminar flow aseptic dispensing machine by means of forked fingers.

4. Method according to claim 1 wherein said temporary plugs are recycled.

5. Temporary plug for implementing a method of packaging freeze dried vaccine in a bypass syringe in which sterilized syringes are disposed in rows in an aseptic dispensing machine, doses of a solution or suspension to be freeze dried are introduced into said syringes, a temporary plug is inserted in the same machine into the mouth of said syringe body in a position allowing communication between the interior of said syringe body and the exterior, said syringes are introduced into a freeze drying machine, the vaccine is freeze dried, at the end of the freeze drying cycle said temporary plug is depressed in a controlled atmosphere in said freeze drying machine into a hermetic sealing position, said syringes are transferred into an aseptic dispensing machine, said temporary plug is removed, an intermediate piston-plug is fitted, the dose of solvent is introduced and an end terminal piston-plug is fitted, said temporary plug comprising a first part adapted to enter at least partially into said syringe body and said passages enabling communication between the interior of said syringe and the exterior environment, a second part adapted to be inserted into said syringe body in a second insertion position of said temporary plug to seal hermetically said syringe body, and a third part adapted to project to the outside in any position of said temporary plug to enable grasping of said temporary plug to remove it from said syringe body.

6. Plug according to claim 5 further comprising on said first part a plurality of ribs between which are passages for vapour and gas.

7. Plug according to claim 6 wherein said first part has a small shoulder whereby said temporary plug may be positioned initially in said syringe body.

8. Plug according to claim 5 wherein said second part has a peripheral rib or lip.

9. Plug according to claim 5 wherein said third part has a peripheral groove enabling it to be grasped by an extractor tool.

* * * * *